(12) United States Patent
Lilge et al.

(10) Patent No.: US 6,514,277 B1
(45) Date of Patent: Feb. 4, 2003

(54) FIBER OPTIC MULTITASKING PROBE

(75) Inventors: Lothar Lilge, Toronto (CA); David Walsh, Waterdown (CA)

(73) Assignee: Photonics Research Ontario, Toronto (CA)

( * ) Notice: Subject to any disclaimer, the term of this patent is extended or adjusted under 35 U.S.C. 154(b) by 0 days.

(21) Appl. No.: 09/329,998

(22) Filed: Jun. 11, 1999

(51) Int. Cl.$^7$ .............................................. A61B 18/22
(52) U.S. Cl. .............................. 607/88; 607/89; 606/10; 606/13; 600/475; 600/478; 422/82.08; 422/82.11
(58) Field of Search ................................ 606/7, 10–18; 600/310–344, 407, 473–476, 478; 607/88, 89; 422/82.05, 82.08, 82.11

(56) References Cited

U.S. PATENT DOCUMENTS

| | | | |
|---|---|---|---|
| 4,735,212 A | | 4/1988 | Cohen |
| 4,799,479 A | * | 1/1989 | Spears ............................ 606/7 |
| 4,981,138 A | | 1/1991 | Deckelbaum et al. |
| 5,082,630 A | | 1/1992 | Partin et al. |
| 5,173,432 A | | 12/1992 | Lefkowitz et al. |
| 5,244,636 A | * | 9/1993 | Walt et al. ................... 600/342 |
| 5,275,160 A | | 1/1994 | Lilge et al. |
| 5,298,741 A | * | 3/1994 | Walt et al. ................... 600/342 |
| 5,353,792 A | | 10/1994 | Lubbers et al. |
| 5,441,530 A | | 8/1995 | Landry et al. |
| 5,460,971 A | | 10/1995 | Gottlieb |
| 5,483,958 A | | 1/1996 | Merberg et al. |
| 5,525,466 A | | 6/1996 | Slovacek et al. |
| 5,582,170 A | * | 12/1996 | Soller .......................... 600/332 |
| 5,779,978 A | | 7/1998 | Hartmann et al. |
| 5,851,225 A | | 12/1998 | Lawandy |
| 6,086,558 A | * | 7/2000 | Bower et al. .................. 607/88 |

FOREIGN PATENT DOCUMENTS

EP           442060 A2     8/1991
EP           470820 A2     2/1992

* cited by examiner

*Primary Examiner*—David M. Shay
(74) *Attorney, Agent, or Firm*—Lynn Schumacher; Ralph Dowell; Hill & Schumacher

(57) ABSTRACT

A multitasking optical fiber probe for collecting dosimeter information from more than one position in a sample. The basic principle of the present invention involves using one or more different sensor zones along the length of the fiber each with a different photoactive constituent having a sufficiently unique emission spectra (spectral or temporal) to enable deconvolution of the emission spectra by the computer and therefore correlation of the detected parameter with the position of the sensor zone along the length of the optical fiber. In the broadest form of the invention the probe is embodied by only one sensor zone located at some point along the length of the fiber spaced away from the end face of the fiber. Probes are provided in which multiple sensor zones are disposed along the length of the fiber and photoactive constituents with sufficiently unique emission spectra (intensity and/or spectral shape which convey the optical information) are used in the different sensor zones so that the different spectra can be deconvoluted so that the contributions from the various etch zones can be distinguished. More than one different photoactive constituent could be incorporated into a single sensor zone for measuring several factors in the vicinity of the sensor zone. In photodynamic therapy applications the probe is isotropic in response and can be employed for all light (300 to 900nm) based medical diagnostics and therapeutics. As an extension the probe can include photosensitiser and molecular oxygen concentrations dosimetry to be used for photodynamic therapy (PDT) treatment monitoring, dosimetry and planning utilizing a mathematical model describing tissue response to PDT.

24 Claims, 8 Drawing Sheets

NORMALIZED GRAPH OF LDS 750 PROBE ISOTROPY

NORMALIZED GRAPH OF LD700 PROBE ISOTROPY

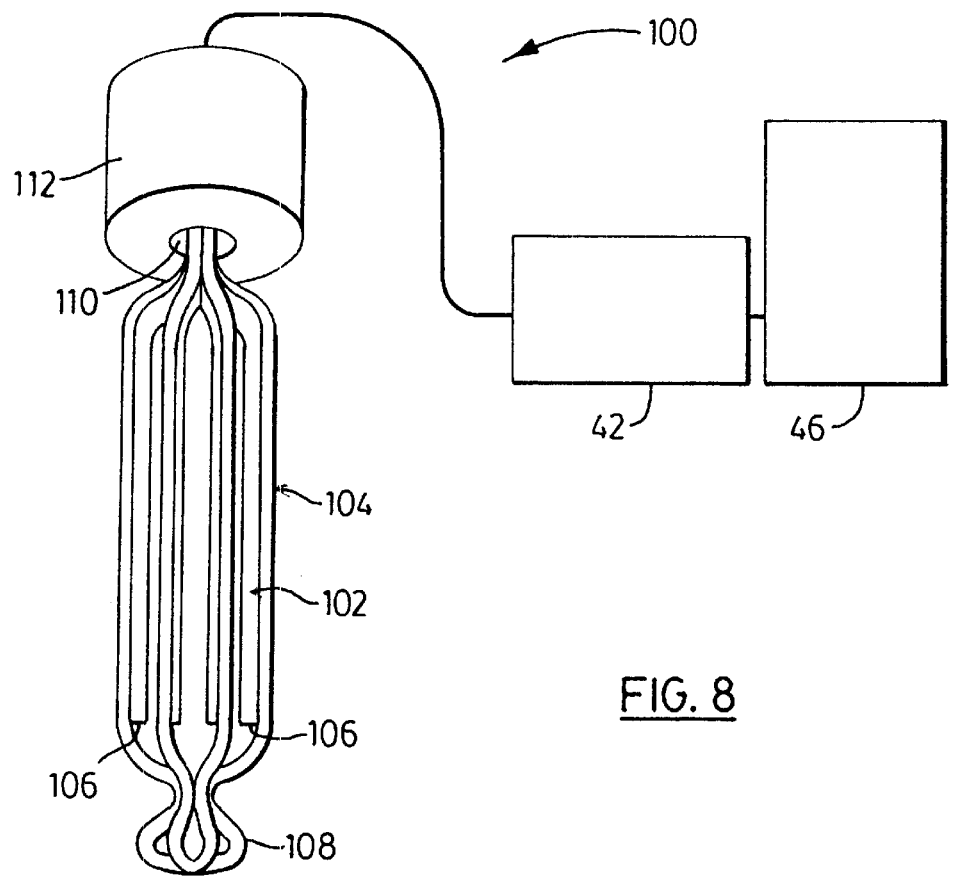
FIG. 8
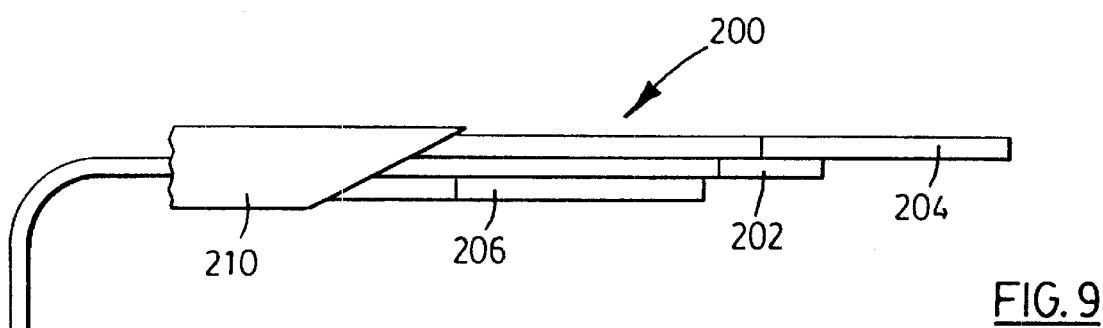
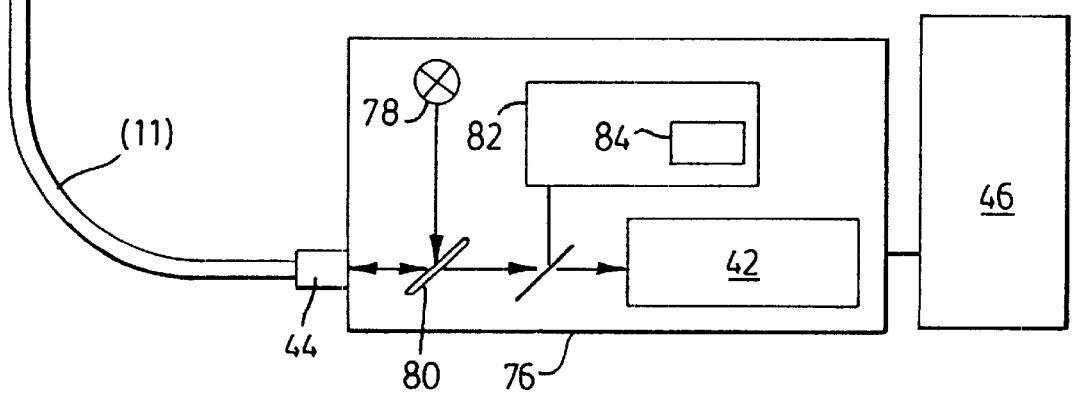
FIG. 9

FIBER OPTIC MULTITASKING PROBE

FIELD OF THE INVENTION

The present invention relates to optical fiber probes for sensing parameters simultaneously at different positions along the probe to provide a spatial profile of the parameters. More particularly, the invention relates to optical fiber probes for measuring multiple dosimetric parameters simultaneously at different positions along the probe in diagnostic and/or therapeutic applications related to photodynamic therapy.

BACKGROUND OF THE INVENTION

Photodynamic therapy (PDT) dosimetry is currently based on two principal approaches, termed explicit and implicit dosimetry as discussed in for example Wilson B C, Patterson M S, Lilge L. (1997), Extrinsic and intrinsic Dosimetry For Photodynamic Therapy; *Lasers in Medical Science* 12: 182–199. For explicit dosimetry the three parameters governing PDT efficacy (fluence-rate, photosensitiser concentration, and molecular oxygen concentration) need to be monitored throughout the treatment volume. However, the current available fiber optic based dosimeters enable detection of parameters only at a single location, requiring several detectors, see for example Lilge L., Molpus K., Hasan T. and Wilson B. C., (1998) Intraperitoneal Photodynamic Therapy In A Murine Xenograft Model Of Human Epithelial Ovarian Carcinoma: Light Dosimetry And Biological Response, *Photochem. Phtobiol.* 83: 281–288, resulting in clinically unacceptable invasive procedures.

As described in previous work, Lilge L., Haw T., Willson B. C. (1993) Miniature Isotropic Optical Fibre Probes For Quantitative Light Dosimetry In Tissue, Phys. Med. Biol. 38: 215–230, fluence-rate detectors need to provide good sensitivity and isotropy of response in order to quantify the light intensity, called fluence-rate, in a turbid media such as tissue. Using fluorescent dyes with a fiber optic provides good response with isotropy provided by the inherently isotropic fluorescence emission by molecules. It was shown that the fluorescence intensity transmitted via the optical fiber to an opto-electronic detector is correlated to the fluence-rate at the position of the fluorophores inside the tissue. However, individual calibration of the optical fiber detector probe response is required prior to use. The efficiency and efficacy of such procedures would be enhanced by being able to monitor the radial dependence of fluence rate, photosensitizer fluorescence and molecular oxygen during the procedure.

Other use of lasers for therapeutic applications is well known, see for example Wilson B C. Wyman Dr, Malon E D, Tracy R, Farrell T (1991) Energy Delivery And Control For Interstitial Laser Hyperthemia And Laser Photocoagulation of Solid Tumors In Vivo; Proc. Soc. Photo-opt. Instr. Eng. 1599: 333–342. Here, the invention provides advantages through measuring the fluence rate profile, or for example, measuring the distribution of exogenous fluorophores.

U.S. Pat. No. 5,082,630 discloses a fiber probe for immuno-testing that uses fluorophore tags bound to an intermediate molecule which in turn is bound to a protein coating on a fiber core. A light beam from the fiber excites fluorescence in the fluorophores and when biomolecules being detected displace the fluorophores the fluorescent intensity decreases thereby indicating the presence of the biomolecules.

U.S. Pat. No. 5,275,160 shows a fiber probe with a single dye contained in a modified tip for radiance dosimetry. U.S. Pat. No. 5,483,958 shows a fiber optic probe using a solid state fluorescent probe joined to the end of the optical fiber.

U.S. Pat. No. 5,173,432 discloses a fiber optic sensor for the detection of $pO_2$ using a luminescent dye encapsulated in a polymer matrix attached to the end of the optical fiber using an $O_2$ permeable membrane.

U.S. Pat. No. 5,441,530 discloses a photochemotherapy dosimeter having a chemical cell at the end of the optical fiber and U.S. Pat. No. 5,851,225 discloses providing a laser fiber probe for PDT applications having modified surface configurations for creating light emission at different wave lengths.

U.S. Pat. No. 5,837,196 discloses using an array of different biosensors comprised of biological binding partners to detect two or more different species of biological partners. This system relies upon a fiber bundle to convey the information to the detector from the distal ends of the fibers.

There is therefore a need for a single optical fiber probe capable of performing several independent tasks simultaneously.

SUMMARY OF THE INVENTION

It is an object of the present invention to provide a multitasking optical fiber probe, capable of measuring the fluence-rate, photosensitizer fluorescence and $pO_2$ at several different positions along the probe and to provide increased information relevant to PDT dosimetry.

It is also an object of the present invention to provide an optical fiber probe that can be employed in other laser based therapeutic applications such as Barrett's esophagus and interstitial laser hyperthermia.

An advantage of the multitasking probe of the present invention is that it can be used to provide the parameters required for PDT for the entire tissue volume in question. The probes of the present invention provide for measurement of a single parameter at multiple locations along the axis of a single optical fiber as well as providing for measurement of multiple parameters at multiple locations along the axis of the fiber.

In one aspect of the invention, there is provided an optical fiber probe comprising an optical fiber and at least one sensor zone spaced from an end of the optical fiber. The at least one sensor zone includes an effective photoactive constituent having an emission spectrum that emits light responsive to the photoactive constituent interacting with a preselected factor with some of the light being coupled into the optical fiber.

In another aspect, the present invention provides a multitasking optical fiber probe, comprising;

an optical fiber; and at least two sensor zones spaced along a length of said optical fiber, each sensor zone including an effective photoactive constituent having an emission spectrum distinguishable in time domain or spectral domain from emission spectra of photoactive constituents in all other sensor zones, each photoactive constituent emitting light responsive to said photoactive constituent interacting with preselected factors with some of the light emitted from each sensor zone being coupled into the optical fiber.

In this aspect of the invention, the preselected factors are selected from the group consisting of radiation incident on said photoactive constituent in preselected wavelength bands and preselected molecules present in a volume adjacent to each sensor zone. The photoactive constituents in the at least two sensor zones may each be selected from the group consisting of fluorophore compounds each having a fluorescent emission spectrum, photoluminescent phosphor compounds each having a phosphorescent emission spectrum, chemiluminescent compounds each having a chemiluminescent spectrum, scintillator compounds each having a scintillator emission spectrum, and any combination thereof.

The present invention also provides a multitasking optical fiber probe apparatus, comprising:

a spectrophotometer;

an optical fiber probe connected to the spectrophotometer, the optical fiber probe including a longitudinal optical fiber, and at least two sensor zones spaced along a length of the optical fiber, each of the sensor zones including an effective photoactive constituent having an emission spectrum distinguishable in time domain or spectral domain from emission spectra of photoactive constituents in all other sensor zones, each photoactive constituent emitting light responsive to said photoactive constituent interacting with preselected factors; and computer control means connected to the spectrophotometer for controlling the spectrophotometer and analyzing optical data from the optical fiber probe.

In another aspect of the invention there is provided a method of detection of factors including radiation and preselected molecules, comprising;

providing an optical fiber having a plurality of sensor zones spaced along a length of said optical fiber, each sensor zone including an effective photoactive constituent having an emission spectrum distinguishable in time domain or spectral domain from emission spectra of photoactive constituents in all other sensor zones, each photoactive constituent emitting light responsive to preselected factors interacting with said photoactive constituent with some of the emitted light being coupled into said optical fiber; and deconvoluting emission spectrum from the photoactive constituent in each of said at least two sensor zones to determine a presence or absence of preselected factors interacting with said photoactive constituent in each sensor zone along the length of the fiber.

BRIEF DESCRIPTION OF THE DRAWINGS

The invention will now be described, by way of non-limiting examples only, reference being had to the accompanying drawings, in which:

FIG. 8 is a perspective view of another embodiment of the fiber optic probe constructed in accordance with the present invention specifically adapted to use in photodynamic therapy in Barrett's esophagus; and FIG. 9 is cross sectional view of another alternative embodiment of a an optical fiber probe in accordance with the present invention.

DETAILED DESCRIPTION OF THE INVENTION

Fiber Optic Probes For Fluence-Rate Dosimetry And Quantification of $pO_2$

Fluence-rate is a physical quantity describing the power density [$W/cm^2$] of the PDT treatment light. Due to multiple scattering of light by biological tissue, the radiation is traveling in all directions. The latter is also called isotropic radiation. To accurately determine the power density at a position P, inside a light scattering medium such as tissue, the unit area is defined by the surface of a sphere with radius of 0.28 cm at position P. The signal measured is fluorescence intensity which is a function of the fluorescence quantum yield of the fluorophore used in the optical fiber and its concentration as well as the fluence-rate of the exciting radiation. The first two parameters are fixed for each detector probe, hence the fluorescence intensity is a direct function of the fluence-rate.

The partial pressure of oxygen inside the tissue being monitored and/or treated is referred to as $pO_2$. This is different from the oxygen saturation in the arterial blood as measured by pulse oxymeters. The oxygen pressure is determined by the supply via the vasculature (or in case of the skin by diffusion from the outside of the skin) and the loss due to metabolic activity of the cells. For PDT molecular oxygen is required. However, PDT results in additional consumption of oxygen and possibly in reduction of supply due to vaso-constriction or obstruction due to hemorrhaging. The molecular oxygen will interact with the phosphor on the optical fiber and allow, next to the phosphorescence decay of the excited triplet state, another non-radiative deactivation mechanism. This interaction will reduce the probability of a phosphorescence event and hence the phosphorescence lifetime. Thus, the concentration of the available oxygen is directly correlated with this non-radiative decay of the triplet state and hence directly correlated with the phosphorescence lifetime.

Figure 1:
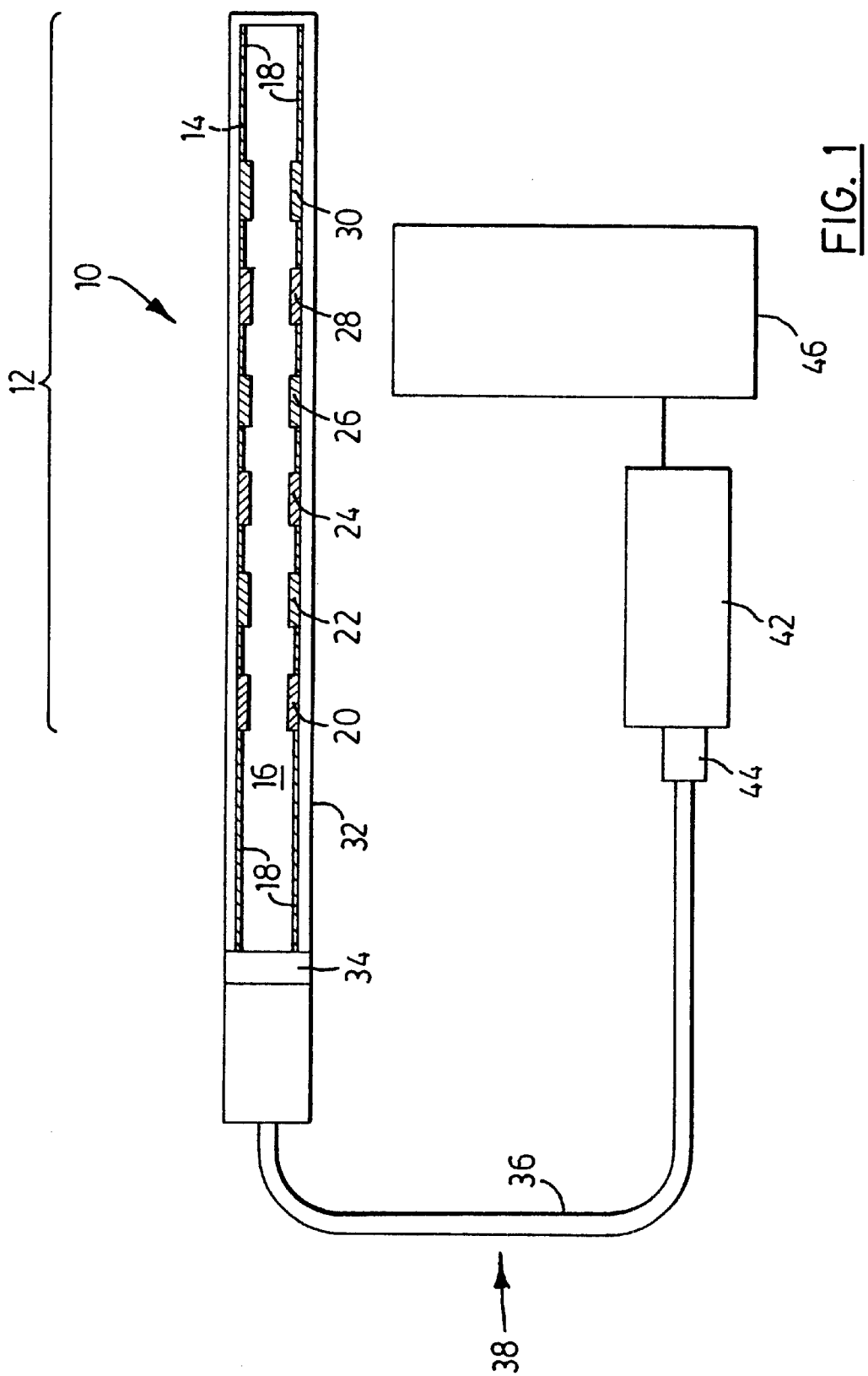
FIG. 1 is a cross sectional view of a fiber optic probe constructed in accordance with the present invention.

Referring to FIG. 1, a fiber optic multitasking probe 10 is shown for fluence-rate dosimetry in turbid media. The probe 10 includes a probe head portion 12 comprising an optical fiber 14 having a core 16 encased by the cladding 18 and several fluorphore filled etch zones 20, 22, 24, 26, 28 and 30. The different fluorophores each preferably have different wavelength sensitivities. A removable translucent cover 32 which slides over the optical fiber 14 prevents leakage of fluorophores from the probe into the tissue while allowing exposure of the fluorophores by the PDT treatment light. Probe 10 also includes an x-ray opaque marker 34 for providing placement verification by x-ray diagnostic tools and a protective cover 36 (for example TEFLON or other optically transparent and physiologically acceptable material) along the length of the fiber portion 38 adjoining the probe head portion 12 to a spectrometer 42. The fiber portion 38 is connected to the spectrometer 42 using an industry standard terminating end 44. The spectrophotometer 42 allows wavelength selection of the emitted light transported through the optical fiber 14 and is connected to a computer 46 for controlling the output of the PDT light source and handling the optical data from the different fluorophore zones.

The PDT treatment light, the intensity of which is the parameter to be measured, is acting as the excitation source for the fluorophore filled etch zones (20, 22, 24, 26, 28 and 30) and originates from a PDT light source spaced away from probe 10. A portion of the fluorescence produced in the fluorophores in each zone is guided via the optical fiber out of the tissue and delivered to the spectrophotometer. To be able to separate the contributions from the various etch zones, fluorophores with sufficiently different emission spectra (intensity and/or spectral shape which convey the optical information) are used. As described above the signal measured (fluorescence intensity) is a function of the fluorescence quantum yield of the fluorophore used in the optical fiber and its concentration (both fixed in each probe) as well as the fluence-rate of the exciting radiation e.g. the PDT treatment light. Hence the fluorescence intensity is a direct function of the fluence-rate.

Figure 2:
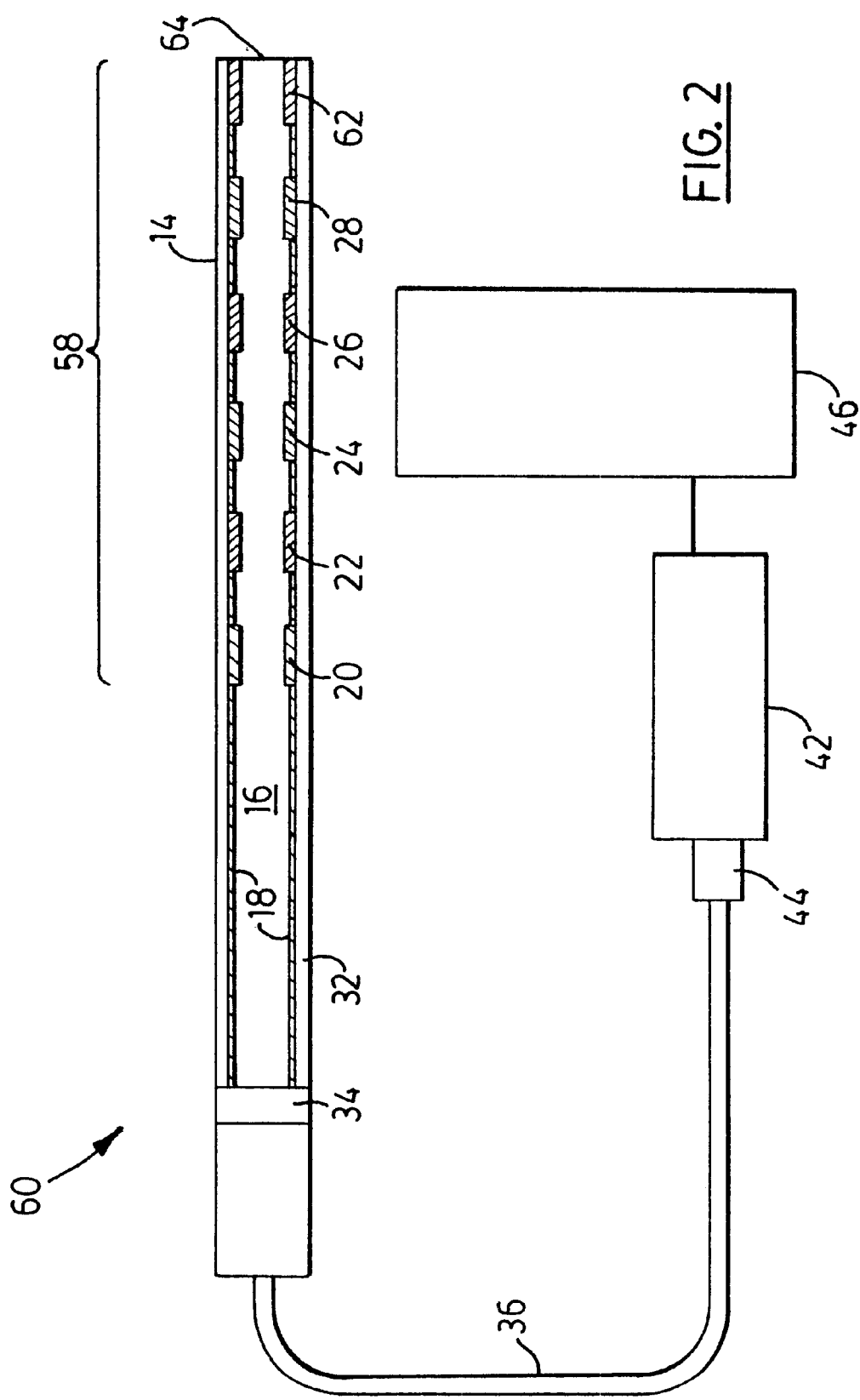
FIG. 2 is a cross sectional view of an alternative embodiment of a fiber optic probe.

FIG. 2 shows a probe 60 similar to probe 10 to provide multitasking for fluence-rate dosimetry in turbid media but modified to provide simultaneously both fluence-rate and photosensitizer quantification. Photosensitizers are exogenous dyes which are administered to a patient for the purpose of treating with photodynamic therapy. Next to generating cytotoxic products upon illumination, the photosensitizer also emits fluorescent light. The probe 60 is designed so that probe head portion 58 includes a fluorophore containing zone 62 placed at the distal end 64 of the probe. The exposed distal end 64 of the fiber 14 enables coupling of the photosensitiser fluorescence into the fiber optical probe 60. The spectra of the emitted fluorescence is significantly different from that of the fluorophores embedded into the fiber itself.

As described above, the fluorophore containing zone 62 is quantifying the fluence-rate at this position. All photosensitizers fluoresce, after being excited by the PDT-treatment light fluence-rate. The photosensitizer fluorescence intensity is given by the excitation fluence rate (measured through fluorophore at position 62 as described above) its fluorescence quantum yield, which is fixed, and the photosenstizer concentration, e.g. the quantity of interest. Hence, the fluorescence intensity is directly correlated with the photosensitizer concentration. Based on the known fluence rate at this position, the known fluorescent quantum yield and the measured fluorescence intensity, the photosensitizer concentration is calculated.

Probe 10 shown in FIG. 1 measures only the fluence-rate in the tissue, while probe 60 shown in FIG. 2 in addition also measures the photosensitizer fluorescence.

Figure 3:
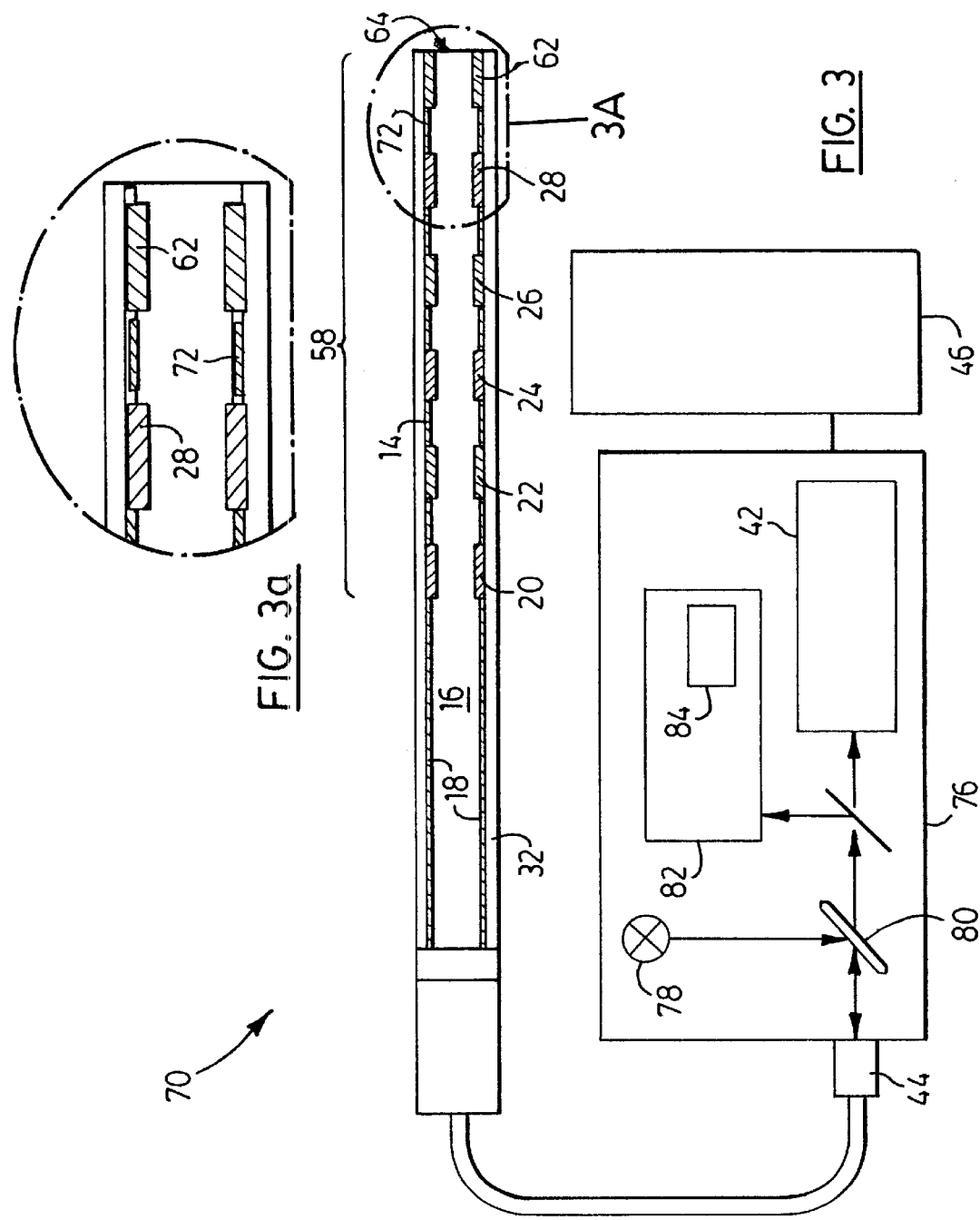
FIG. 3 is cross sectional view of another alternative embodiment of a fiber optic probe.

For quantification of $pO_2$ the phosphorescence lifetime may be employed (see for example Lo L W, Koch C. J, Wilson D F (1996) Calibration of Oxygen-Dependent Quenching Of The Phosphorescence Of Pd-mesotetra (4-Cabocyphynyl) Porphine: A Phosphor With General Application Of Measuring Oxygen and Vanderkooi et al. J. of Biol. Chem. Vol 262 5476–82 1987). Referring now to FIG. 3, there is shown a fiber optic multitasking probe 70 for simultaneous fluence-rate and $pO_2$ dosimetry in turbid media. The probe 70 comprised of the optical core is similar to probes 10 and 60 but is modified so the optical fiber core 16 includes a sensor zone 72 comprising a photoluminescent phosphor between the distal end portion 64 containing fluorophore zone 62 and fluorophore zone 28, see the blowup in FIG. 3. A control unit 76 comprises a light source 78 for phosphor excitation (for example any source emitting in the blue that can be activated very rapidly, such as an LED), a dichroic beam splitter 80 to separate selection detector 82 and fast opto-electronic detector 84 for lifetime quantification. In the embodiment in which the probe 70 operates as a dual fluence-rate and $pO_2$ detector, the control unit 76 will also house a spectrophotometer 42. Other embodiments of the probe may include several different phosphor containing sensor zones along the fiber 14 each with its own spectral signature or alternatively probes may be produced in which all the zones contain different phosphors if the application of the probe is only for measuring $pO_2$ whether or not photosensitizer concentrations are being measured.

When photoluminescent phosphors are used the optical information is encoded in the spectral shape and lifetime. Table 1 provides an exemplary, non-limiting list of phosphors that may be used with the fiber probes. The phosphors are embedded in a membrane which is brought into contact with the core of the optical fiber and exposed to the tissue. Some of the light emitted by the phosphors is transmitted down the fiber 14 to be interrogated at the spectrometer 42 and computer 46. The fluorescence lifetime of triplet oxygen measurement is made using a short pulse excitation (~100 nsec) followed by nanosecond time resolution of the decay. The excitation wavelength is provided by the spectrophotometer 42 in control unit 76 and is absorbed by all employed phosphors. The phosphors used are selected on the basis that they exhibit sufficiently unique emission spectra to provide spatial resolution and quantification of lifetimes. Cross talk between the fluorescence and phosphorescence measurements is avoided because the phosphors do not absorb at the wavelengths corresponding to the PDT treatment wavelength. Therefore the light used in the PDT does not induce any phosphorescence. Also, the fluorescence decay being several orders of magnitude faster than the phosphorescence, does not affect the phosphorescence lifetime after a few nsec. However, this approach requires that illumination with the PDT treatment light needs to be suspended during phosphorescence measurements.

A common feature of the different embodiments of the multitasking probe disclosed herein are the different spaced sensor zones along the length of the optical fiber filled with a photoactive constituent. Methods of generating the sensor zones include, but are not limited to; etching of the original material either mechanically, chemically or optically, and applying a photoactive constituent doped material (polymethylmethacrylate (PMMA), cyanoacrylate and others); diffusion of the photoactive constituent, such as fluorophores, into the core material, for example by heating and chemically softening the raw material. The depth of the etched zone ranges from 0.20 micrometer to full core diameter. For example, a probe can be produced by etching one or more zones in a fiber by laser induced plasma or mechanical abrasion using miniature tools and filling of the etched zone(s) by applying a fluorophore doped polymer mix (the latter may be comprised of either the optical fiber monomer or a cyanoacrylate adhesive) and polishing the fiber upon completion of the polymerization process. The probes preferably use plastic optical fibers for ease of manufacturing and safety of handling outside and inside the patient.

The basic principle of the present invention involves using one or more different sensor zones along the length of the fiber each with a different photoactive constituent having a sufficiently unique emission spectra (spectral or temporal) to enable deconvolution of the emission spectra by the computer and therefore correlation of the detected parameter with the position of the sensor zone along the length of the optical fiber. In the broadest form of the invention the probe is embodied by only one sensor zone located at some point along the length of the fiber spaced away from the end face of the fiber. The important feature that enables operation of the probe as a sensor for detecting factors at any given position along the length of the fiber is to incorporate the photoactive constituent into the sensor zone in the bulk of the fiber or on the fiber surface located at the given position along the fiber. Whether on the surface of the fiber or incorporated in the bulk of the fiber the key is the photoactive constituent is incorporated in such a way so that a portion of the light emitted by the photoactive constituent responsive to interaction of the latter with the factor of interest is guided via the optical fiber out of the tissue and delivered to the spectrophotometer. In the preferred embodiments in which multiple sensor zones are disposed along the length of the fiber, photoactive constituents with sufficiently unique emission spectra (intensity and/or spectral shape which convey the optical information) are used in the different sensor zones so that the different spectra can be deconvoluted so that the contributions from the various etch zones can be distinguished. More than one different photoactive constituent could be incorporated into a single sensor zone for measuring several factors in the vicinity of the sensor zone.

Figure 4:
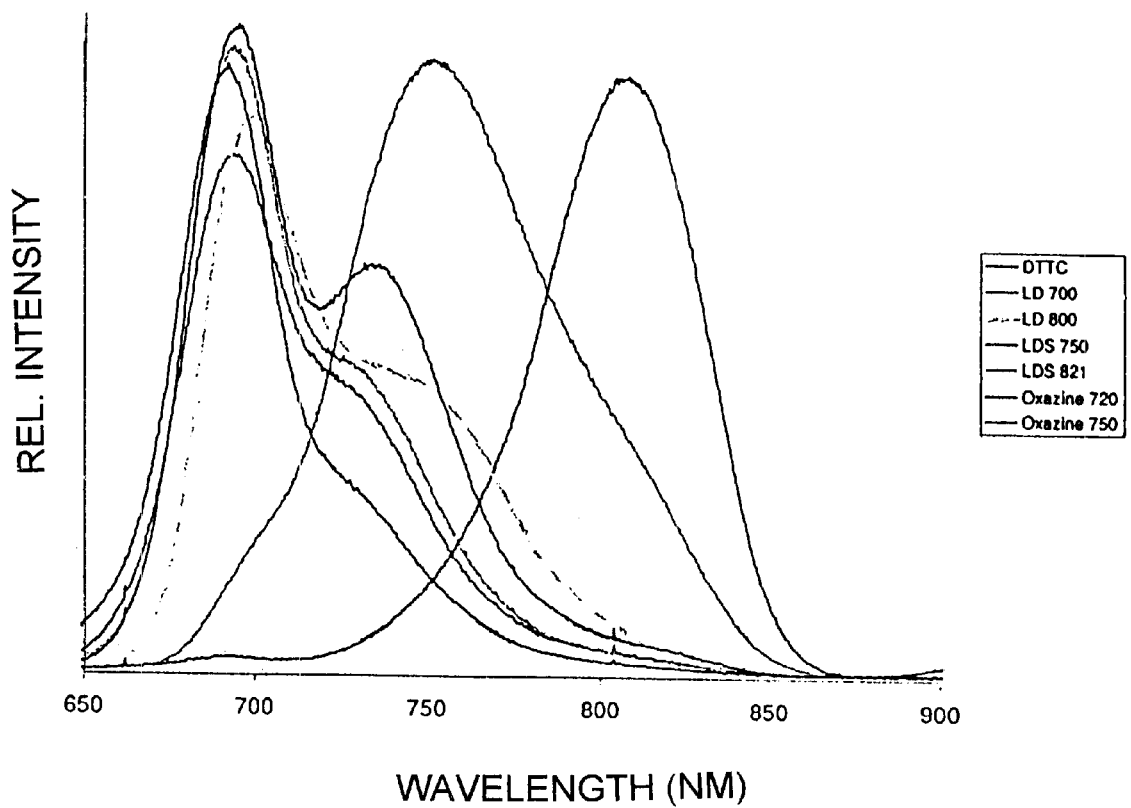
FIG. 4 is a plot of fluorescence emission intensity versus wavelength for seven exemplary fluorophores used in the multitasking probes.

Examples of seven different fluorophores and their spectral properties that may be used in the present invention for PDT applications are shown in Table 2. All fluorophores absorb the PDT treatment wavelength, here 630 to 690 nm, but show sufficiently different emission spectra so the detected spectra can be numerically deconvoluted to extract the intensity of each fluorophore. Thus the fluence-rate at all points doped with fluorophore can be extracted, one of which will be close to the distal end (see FIG. 2). The fluorescence emission of the seven example fluorophores used in the multitasking probes are shown in FIG. 4. All spectra were measured in an optical fiber containing only one active sensor. It will be understood that the list of candidate fluorophores in Table 2 is not exhaustive and other fluorophores being currently developed may be employed in the present fluence rate fiber optical probes. For use in other light (300–900 nm) based therapeutics, the fluorophore absorption needs to match the treatment wavelength. For example, in the case of interstitial laser hypothermia (ILH) discussed hereinafter, a fluorophore is required that is able to absorb between 800 to 900 nm.

Figure 5A:
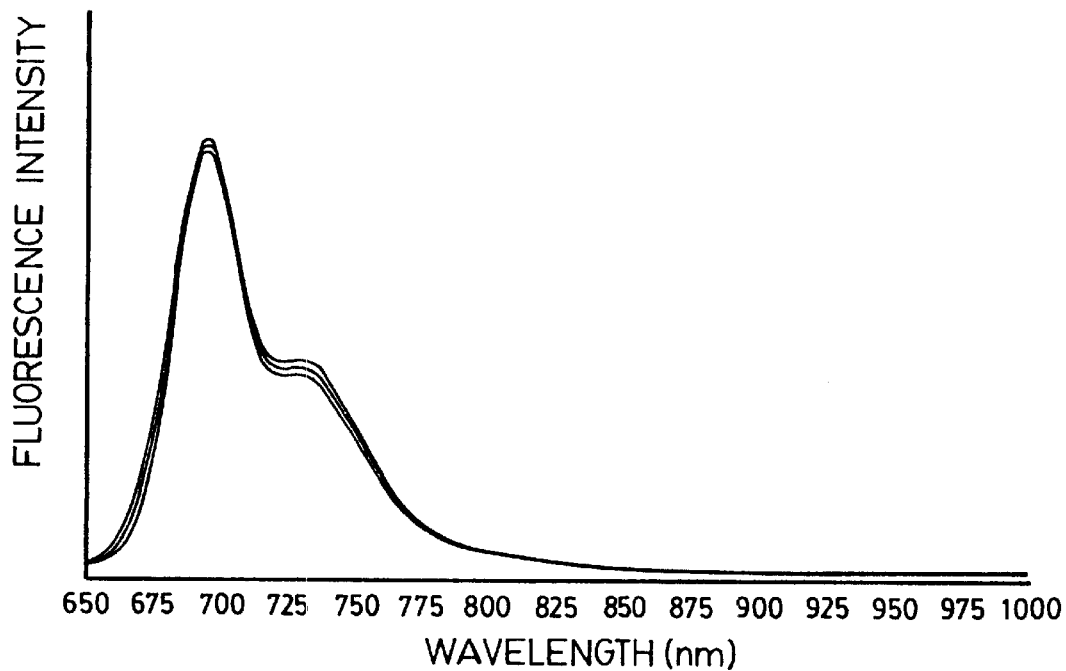
FIG. 5a is a plot of fluorescence intensity verses wavelength giving the average normalized fluorescence emission spectra of a sensor illuminated from different azimuth angles.
Figure 5B:
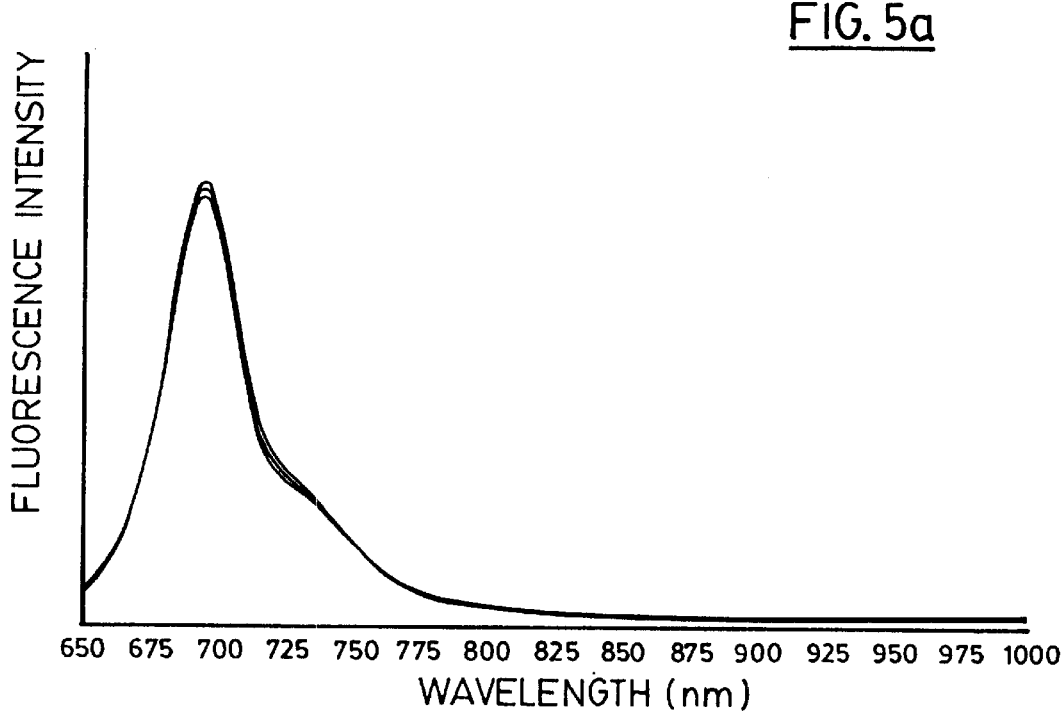
FIG. 5b is a plot of fluorescence emission intensity versus wavelength giving the normalized fluorescence emission spectra of 10 individually manufactured probes, showing independence of manufacturing, hence, responsivity calibration for each sensor is possible.

FIG. 5a shows the average normalized fluorescence emission spectra of a sensor illuminated from different azimuth angles, showing that the emission spectra shape is independent of azimuth angle of illumination. FIG. 5b shows the normalized fluorescence emission spectra of ten individually manufactured multitasking probes, showing independence of manufacturing, and hence, responsivity calibration for each sensor is possible.

Figure 6A:
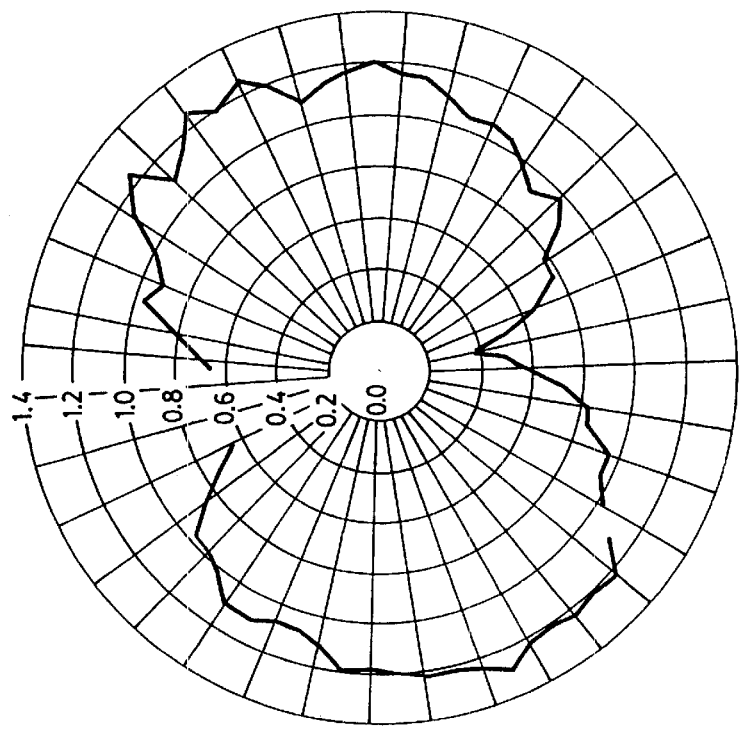
FIG. 6 shows a polar diagram showing the isotropy of detector response.
Figure 6:
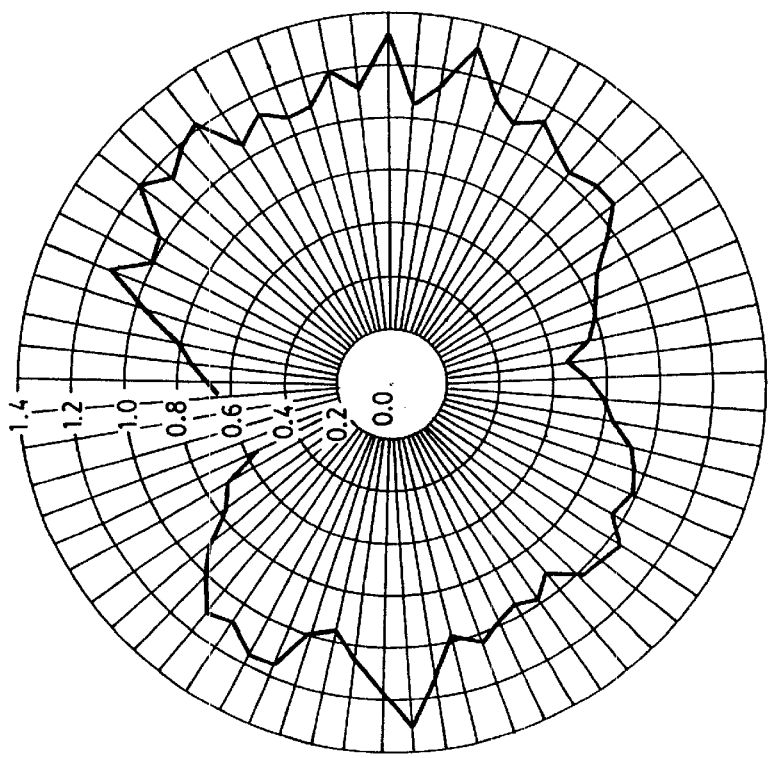

FIG. 6 shows a typical polar diagram showing the isotropy of detector response. The reduction of responsivity in the forward and backward direction of the fiber is due to shielding of the sensor by the fiber itself. This shielding encompasses only 6% of the total surface volume.

Figure 7:
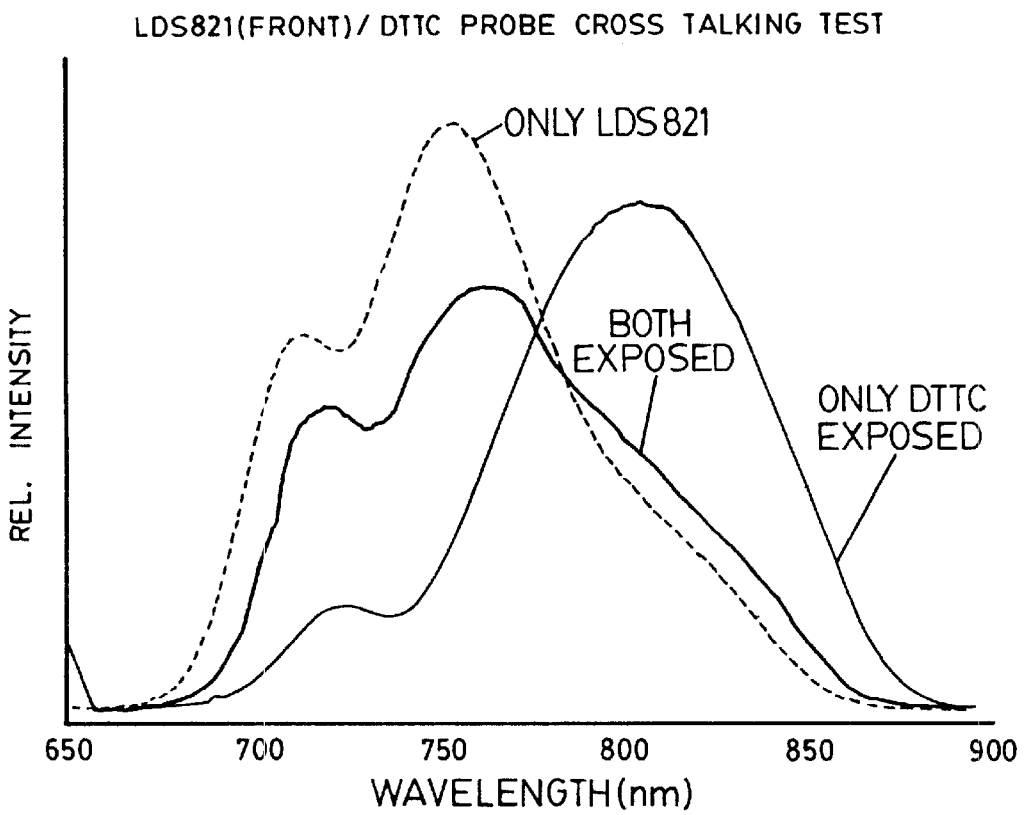
FIG. 7 shows the emission spectra of a fiber optical detector probe comprised of 2 sensors for individually exposed sensors and combined exposure of both sensors.
Figure 7A:
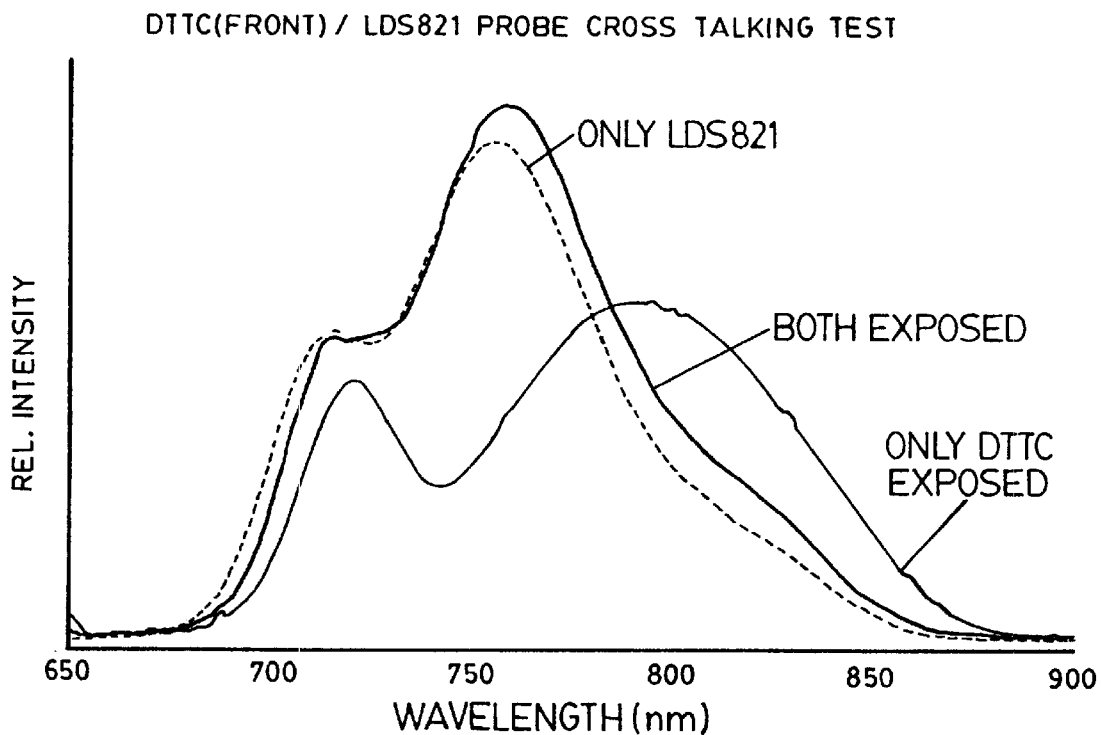

FIG. 7 shows the emission spectra of an optical fiber detector probe comprised of 2 sensors for individually exposed sensors and combined exposure of both sensors. The data shown in FIGS. 5 to 7 illustrates the efficacy of the multitasking probes disclosed herein.

While the optical fiber probes have been described using fluorophores and photoluminescent phosphors as the photoactive constituents in the sensor zones, it will be understood that other materials could be used depending on the factor(s) being detected. For example, sensor zone containing chemiluminescent compounds as the photoactive constituent may be used for the detection of adenosine triphosphate (ATP) and for the detection of hydrogen peroxide. In either case the chemical to be detected supplies the energy required for photon emission. Further examples for the use of chemiluminescence are in the detection of choline and phosphaolipase D activity, phosphate ions and immunoenzymes given by Ruach P, Ferri En Girotti S, Rauchova H, Carrea G, Bovara R, Fini F Analyytical Biochem. 245 133–40 1997, Nakamura H, Ikebukuro K, NcNiven S, Karube I, Yamamoto H, Hayashi K, Suzuki M Kubo M, in Biosensors And Bioelectronics 12 956–66, 1997; and Ospipov A, Aeitseva N V, Egorov E M, Biosensors And Bioelectronics 11 881–7, 1996, respectively. The chemiluminescent compound may be provided by using choline oxidase (ChO) and horseradish peroxidase (HRP) immobilized on Eupergit C (polymer beads of methacrylamide, -methylene-bis-methacrylamide, and allyl-glycidyl-ether) or be catalyzed by arthromyces ramosus peroxidase. In embodiments employing chemiluminescent compounds the unique emission spectrum and intensity characteristic of each chemiluminescent reaction encodes the spatial location and concentration information.

Additionally, for applications of the present invention involving measurement of radioactivity, the photoactive constituents in some or all of the sensor zones would be scintillator compounds in which the unique intensity of each scintillator compound encodes the information. Organic scintillators may be used with compatible optical fibers in producing the probes.

The optical fiber probes of the present invention may be used in a variety of applications in addition to PDT in mammals. For example, they may be used as environmental sensors for use in normally unaccessible areas. The length of the fibers may be as long as required for use in, for example, bodies of water as environmental sensors where pH is being measured as function of water depth. The fibers constructed for use as radiation detectors may be wrapped around pipes and the like and radioactive leaks may be detected since the optical controller deconvolutes the optical data to correlate the emission spectra with the spatial location of the photoactive constituent along the fiber. The length of the photoactive constituent along the fiber will be given by the required spatial resolution of the application.

Photodynamic Therapy in Barrett's Esophagus or Solid Tumors

The present invention provides two specific fiber optic probe systems for the treatment of Barrett's esophagus and interstitial treatment of tumors. Referring to FIG. 8, an applicator 100 is shown for the treatment of Barrett's esophagus. Probe 100 comprises a cage 102 made of superelastic wires 104 with multitasking optical probes 106 mounted on the cage wires. The applicator 100 optionally may include a bulbous end portion 108 that enables anchoring of the device at the gastro-esphageal-junction. The probes 106 are guided through the gastroscope 112 and are connected to the spectroscope 42 and data is processed in the CPU 46. The wires 104 are made out of superelastic metals, such as nitenol wire. The cage applicator 100 is introduced via the working channel 110 of a standard gastroscope 112 and once in the lumen of the esophagus the cage expands the esophagus to enable homogenous illumination of the esophagus, see Overholt B. F., Panjehpour M. (1996), Photodynamic Therapy In Barrett's Esophoagus; J. Clin. Laser Med. Surg. 14: 245–249. In one embodiment eight 0.5 mm diameter wires comprise the cage 102. The total diameter of the cage and the probes is about 2.8 mm.

An applicator for interstitial tumor treatment is shown at 200 in FIG. 9. Applicator 200 comprises a cylindrical isotropic light emitter 202 and two multitasking probes 204 and 206. Light emitter 202 is preferably an optical fiber diffuser which may emit light having a uniform intensity distribution along the length of the diffuser. The two probes 204 and 206 measure the fluence-rate gradient at 2 different positions in the glow field of the isotropic emitter probe 202. These three optical fibers are combined and introduced via a single hypodermic needle 210. The probes are connected to the spectrograph 42 and the data evaluated via CPU 46. The size between the individual detector elements is selected to be comparable to the mean free path of the photons to be measured in the tissue. Hence, the detector is not integrating too much over the gradient of the fluence-rate.

In one embodiment a multitasking probe 204 is located at the proximal end portion of the applicator 200 and a second probe 206 is located at the distal end portion of the applicator with both probes parallel to the axis of the cylindrical source 202. The radial dependence of the three parameters, fluence-rate, photosensitizer concentration and molecular oxygen are those measured during the procedure. In this arrangement the ovid shaped fluence rate profiles generated by the cylindrical source in the target tissue are measure along the long axis of the distribution. The total outer diameter of the assembly is preferably less than 1 mm, where the source has an outer diameter of less than 0.5 mm and the two detectors are 0.25 mm in diameter.

The multitasking probes of the present invention are very advantageous over previous probes because they can be used to provide the parameters required for PDT for the entire tissue volume in question. The multitasking probes disclosed herein can provide for measurement of a single parameter at multiple locations along the axis of a single optical fiber as well as providing for measurement of multiple parameters at multiple locations along the axis of the fiber.

The foregoing description of the preferred embodiments of the invention has been presented to illustrate the principles of the invention and not to limit the invention to the particular embodiment illustrated. It is intended that the scope of the invention be defined by all of the embodiments encompassed within the following claims and their equivalents.

TABLE 1

| Phosphore | Excitation maximum | Solvent |
|---|---|---|
| Pd Coproporphyrin I | 394 nm | DMSO |
| Pd Coproporphyrin III | 398 nm | DMSO |
| Pd TPPS4 | 408 nm | Acetone |
| Pd tetra(N-methyl-4-pyridyl)porphine | 425 nm | DMSO |

TABLE 2

| fluorophore | used solvent | absorption peak [nm] | fluorescence peak [nm] |
|---|---|---|---|
| DTTC | DMSO | 772 | 802 |
| LD 700 | DMSO | 598/648 | 697 |
| LD 800 | DMSO | 626/686 | 700 |
| LDS 750 | MeOH | 580 | 696 |
| LDS 821 | DMSO | 601 | 754 |
| Oxazine 720 | DMSO | 636 | 694 |
| Oxazine 750 | DMSO | 668 | 694/735 |

Therefore what is claimed is:

1. An optical fiber probe apparatus for measuring dosimetric parameters, comprising;

an optical fiber including at least two sensor zones spaced along a length of said optical fiber, each sensor zone including an effective photoactive constituent having an emission spectrum distinguishable in time domain or spectral domain from emission spectra of photoactive constituents in all other sensor zones, each photoactive constituent emitting light responsive to preselected factors external to the optical fiber interacting with said photoactive constituent with some of the light emitted by each photoactive constituent being coupled into said optical fiber.

2. The optical fiber probe apparatus according to claim 1 wherein the sensor zones are defined by diffusing the photoactive constituent into the optical fiber at spaced locations along the length of the optical fiber.

3. The optical fiber probe apparatus according to claim 1 including an optical controller, wherein a proximal end portion of the optical fiber is connected to said optical controller, said sensor zones being spaced from a distal end portion of the optical fiber, and wherein said optical controller includes a spectrophotometer means optically coupled to said optical fiber, said spectrophotometer means being connected to processing means for deconvoluting emission spectrum from the photoactive constituent in each of said at least two sensor zones to measure said dosimetric parameters along the length of the fiber.

4. The optical fiber probe apparatus according to claim 3 wherein said optical controller includes an effective light source for excitation of photoactive constituents comprising photoluminescent phosphor compounds.

5. The optical fiber probe apparatus according to claim 4 including computer control means connected to the spectrophotometer means and the light source for controlling the spectrophotometer means and an output of the light source and for deconvoluting the emission spectra from the photoactive constituents in each sensor zone and for analyzing light coupled into said optical fiber from a distal end face thereof.

6. The optical fiber probe apparatus according to claim 5 wherein the optical fiber probe is produced from a physiologically compatible material for insertion into mammalian tissue, wherein the computer control means deconvolutes optical data transmitted from the sensor zones to obtain dosimetric parameters in a mammalian tissue along the length of the optical fiber probe.

7. The optical fiber probe apparatus according to claim 6 wherein the dosimetric parameters include fluence rates calculated from emission spectra from the sensor zones in which the photoactive constituent is a fluorophore, $pO_2$ calculated from emission spectra from the sensor zones in which the photoactive constituent is a photoluminescent phosphor, and photosensitizer concentration calculated from fluorescence radiation incident on said distal end face emitted by photosensitizers.

8. The optical fiber probe apparatus according to claim 1 wherein the photoactive constituent in the at least one sensor zone is selected from the group consisting of fluorophore compounds each having a fluorescent emission spectrum, photoluminescent phosphor compounds each having a phosphorescent emission spectrum, chemiluminescent compounds each having a chemiluminescent emission spectrum, scintillator compounds each having a scintillator emission spectrum, and any combination thereof.

9. The optical fiber probe apparatus according to claim 8 wherein said preselected factors are selected from the group consisting of radiation incident on said photoactive constituent in preselected wavelength bands and preselected molecules present in a volume adjacent to each sensor zone.

10. The optical fiber probe apparatus according to claim 9 wherein the photoactive constituents in the two or more sensor zones are each selected from the group consisting of fluorophore compounds each having a fluorescent emission spectrum, photoluminescent phosphor compounds each having a phosphorescent emission spectrum, chemiluminescent compound compounds each having a chemiluminescent emission spectrum, scintillator compounds each having a scintillator emission spectrum, and any combination thereof.

11. The optical fiber probe apparatus according to claim 10 wherein the photoactive constituent in at least some of the sensor zones includes a preselected quantity of an effective fluorophore compound, wherein the fluorophore compound in each sensor zone has a fluorescence spectrum different from the fluorescence spectra of the fluorophore compounds in the other sensor zones.

12. The optical fiber probe apparatus according to claim 11 wherein the photoactive constituent in at least some of the sensor zones includes a preselected quantity of an effective photoluminescent phosphor compound, wherein the photoluminescent phosphor compound in each sensor zone has a phosphorescence lifetime different from the phosphorescence lifetimes of the photoluminescent phosphor compounds in the other sensor zones, and wherein the spectrophotometer includes an effective light source for activating excitation of photoactive constituents comprising photoluminescent phosphor compounds.

13. The optical fiber probe apparatus according to claim 12 wherein the sensor zones are defined by spaced circumferential slots formed in an outer cladding of said optical fiber, the photoactive constituents being contained in said slots.

14. A device for photodynamic therapy, comprising:
an elongate isotropic light source for emitting light for photodynamic therapy, the isotropic light source having a length and opposed ends;
a multitasking optical fiber probe adjacent to said elongate isotropic light source, the multitasking optical fiber probe including an elongate optical fiber with a plurality of sensor zones spaced along a length thereof, each sensor zone including an effective photoactive constituent having an emission spectrum distinguishable in time domain or spectral domain from emission spectra of photoactive constituents in all other sensor zones, each photoactive constituent emitting light responsive to said photoactive constituent interacting with preselected factors, the optical fiber having a length longer than the isotropic light source and extending beyond the opposed ends of said isotropic light source;
computer control means for controlling the isotropic light source and calculating preselected dosimetric parameters along the length of said optical fiber from light transmitted along said optical fiber probe.

15. The device according to claim 14 wherein the photoactive constituents in each of the plurality of sensor zones are selected from the group consisting of fluorophore compounds each having a fluorescent emission spectrum, photoluminescent phosphor compounds each having a phosphorescent emission spectrum, and any combination thereof.

16. The device according to claim 15 wherein the optical fiber has a distal end face adapted to couple said optical fiber to radiation incident on said distal end face.

17. The device according to claim 16 wherein the dosimetric parameters include
fluence rates calculated from emission spectra from the sensor zones in which the photoactive constituent is a fluorophore,
$pO_2$ calculated from emission spectra from the sensor zones in which the photoactive constituent is a photoluminescent phosphor, and
photosensitizer concentration calculated from fluorescence radiation incident on said distal end face emitted by photosensitizers.

18. The device according to claim 16 including at least two multitasking optical fiber probes, one being located on one side and extending beyond one of said opposed ends of the isotropic light source and the other being located on another side of the isotropic light source and extending beyond the other opposed end of the isotropic light source.

19. A device for treatment of Barrett's esphoagus, comprising:
an elongate wire cage made of flexible wires, an elongate light source for photodynamic therapy adjustably extendable along a longitudinal axis of said elongate cage, said wire cage having an expandable diameter;
at least some of the flexible wires having a multitasking optical fiber probe attached thereto, each multitasking optical fiber probe including an elongate optical fiber with a plurality of sensor zones spaced along a length thereof, each sensor zone including an effective photoactive constituent having an emission spectrum distinguishable in time domain or spectral domain from emission spectra of photoactive constituents in all other sensor zones, each photoactive constituent emitting light responsive to said photoactive constituent interacting with preselected factors including radiation incident on said sensor zones and preselected molecules; and
computer control means for controlling the light source and calculating fluence rates along the length of said optical fiber from emission spectra from the photoactive constituents in the plurality of sensor zones.

20. The device according to claim 19 wherein the photoactive constituents in each of the plurality of sensor zones are selected from the group consisting of fluorophore compounds each having a fluorescent emission spectrum, photoluminescent phosphor compounds each having a phosphorescent emission spectrum, and any combination thereof.

21. The device according to claim 20 wherein the dosimetric parameters include
fluence rates calculated from emission spectra from the sensor zones in which the photoactive constituent is a fluorophore,
$pO_2$ calculated from emission spectra from the sensor zones in which the photoactive constituent is a photoluminescent phosphor, and
photosensitizer concentration calculated from fluorescence radiation incident on a distal end face of the optical fiber emitted by photosensitizers.

22. The device according to claim 20 wherein said wire cage includes a bulbous distal end portion for anchoring the cage at a gastro-esphageal-junction of a patient.

23. The device according to claim 22 including a gastroscope, wherein the wire cage is contained in a passageway in the gastroscope, including adjustment means for moving the wire cage in and out of the gastroscope, wherein when the wire cage is moved out of the gastroscope and into the lumen of the esophagus the cage expands the esophagus.

24. The device according to claim 23 wherein said wires are made out of superelastic metals.

* * * * *